United States Patent [19]

Gurske

[11] 4,319,976
[45] Mar. 16, 1982

[54] ELECTROPHORETIC TECHNIQUE FOR SEPARATING SERUM PROTEINS AND IMPROVED ELECTROPHORETIC GEL FOR USE THEREIN

[75] Inventor: William A. Gurske, Placentia, Calif.

[73] Assignee: Beckman Instruments, Inc., Fullerton, Calif.

[21] Appl. No.: 226,566

[22] Filed: Jan. 19, 1981

[51] Int. Cl.³ ............................................. G01N 27/26
[52] U.S. Cl. ........................... 204/180 G; 204/299 R; 536/3; 23/230 B
[58] Field of Search ...................... 204/180 G, 299 R; 260/122; 23/230 B; 536/3, 4, 5, 6

[56] References Cited

U.S. PATENT DOCUMENTS

| | | | |
|---|---|---|---|
| 3,527,712 | 9/1970 | Renn et al. | 204/180 G X |
| 3,947,352 | 3/1976 | Cuatrecasas et al. | 204/122 X |
| 3,956,272 | 5/1976 | Tixier | 536/3 X |
| 3,956,273 | 5/1976 | Guiseley | 536/3 X |
| 3,959,251 | 5/1976 | Porath et al. | 536/3 X |

*Primary Examiner*—Arthur C. Prescott
*Attorney, Agent, or Firm*—R. J. Steinmeyer; J. E. Vanderburgh; Robert S. Frieman

[57] ABSTRACT

An electrophoretic gel of the type comprising a polysaccharide. The electrophoretic gel is characterized in that it further comprises an acid polysaccharide and salts thereof, wherein the acid moiety of the acid polysaccharide comprises at least one carboxyl group.

An improved electrophoretic technique for assaying the relative distribution of proteins of the type wherein a sample to be assayed is applied to an electrophoretic gel and the electrophoretic gel is electrophoresed. The electrophoretic technique is characterized in that the above described electrophoretic gel is employed therein.

36 Claims, No Drawings

ELECTROPHORETIC TECHNIQUE FOR SEPARATING SERUM PROTEINS AND IMPROVED ELECTROPHORETIC GEL FOR USE THEREIN

BACKGROUND OF THE INVENTION

1. Field of the Invention

The instant invention pertains to an electrophoretic technique for separating serum proteins and to an electrophoretic gel for use therein.

2. Description of the Prior Art

Electrophoretic techniques for separating serum proteins and electrophoretic gels for use therein are well known to those skilled in the art. Cawley, *Electrophoresis and Immunoelectrophoresis*, Little, Brown and Company, Boston, Mass. (1969). In general, electrophoretic gels employed for separating serum proteins are of the type comprising a polysaccharide. A buffer having a basic pH is also commonly present in these electrophoretic gels.

Typical polysaccharides employed in prior art electrophoretic gels include, but are not limited to, starch, cellulose acetate, agar, agarose, and combinations thereof.

Typical buffers having a basic pH employed in prior art electrophoretic gels include, but are not limited to, the basic pH buffers which are set forth in Table I of Cawley, supra, pp. 331-332.

One problem present in prior art electrophoretic techniques for separating serum proteins is that it takes a substantial amount of time (on the order of 30 minutes and longer) for the serum proteins to become fixed, i.e., capable of visual observation. This relatively long protein fixation period makes the prior art serum electrophoretic technique a time consuming procedure.

Accordingly, it would be very desirable to have an electrophoretic technique for the separation of serum proteins wherein the protein fixation period is relatively short. Such an improved electrophoretic technique for separating serum proteins would enable the clinical laboratory to supply vital information to the diagnostician in a shorter period of time.

SUMMARY OF THE INVENTION

In accordance with the present invention there is provided an improved electrophoretic technique for separating serum proteins wherein one is capable of obtaining a rapid fixation of serum proteins. The electrophoretic technique of this invention is of the type wherein a sample to be assayed is applied to an electrophoretic gel and the electrophoretic gel is electrophoresed. The improved electrophoretic technique of the instant invention is characterized in that a novel electrophoretic gel is employed therein. The electrophoretic gel is characterized in that it further comprises an acid polysaccharide and the salts thereof, wherein the acid moiety thereof comprises at least one carboxyl group. It is the presence of the acid polysaccharide as well as the salts thereof in the electrophoretic gel which enables one to obtain the rapid fixation of serum proteins.

Still other features and attendant advantages of the present invention will become apparent to those skilled in the art from a reading of the following detailed description of the preferred embodiments.

DESCRIPTION OF THE PREFERRED EMBODIMENTS

Acid polysaccharides capable of use in the instant invention include, but are not limited to, arabic acid, tragacanth acid, kahya acid, alginic acid, pectic acid, and linseed acid. The preferred acid polysaccharide is arabic acid.

Salts of acid polysaccharides capable of use in the instant invention include, but are not limited to, the sodium, potassium, calcium, and magnesium salts thereof. Examples of such acid polysaccharide salts include, but are not limited to, arabic gum acid, tragacanth gum acid, khaya gum acid, alginic gum acid, pectic gum acid, and linseed gum acid.

Polysaccharides which can preferably be employed in the electrophoretic gel of the instant invention are agar and agarose. The agarose can be either low electroendosmosis agarose, medium electroendosmosis, or high electroendosmosis agarose. More preferably, the polysaccharide employed in the electrophoretic gel of the instant invention is high electroendosmosis agarose.

Preferably, the buffer employed in the instant invention has a pH of about 7 to about 10. More preferably the buffer has a pH of about 8 to about 9.

The electrophoretic gel of the instant invention can optionally further comprise a preservative agent. Typical preservative agents include, but are not limited to, antibiotics, halogenated organic compounds, and inorganic compounds. One readily available preservative agent capable of use herein is sodium azide.

The electrophoretic gel of the instant invention can also optionally contain an alkylpolyol having 2 to 6 carbon atoms and 2 to 4 hydroxyl groups. Suitable alkylpolyols which can be used herein include, but are not limited to, ethylene glycol, propanediol, butanediol, pentanediol, and glycerol. Preferably, the alkylpolyol has 2 to 4 carbon atoms.

The exact concentrations of the various constituents employed in the electrophoretic gel of the present invention are not critical. However, the electrophoretic gel of the instant invention preferably comprises from about 0.4 to about 1.5 percent weight/volume high electroendosmosis agarose; from about 0.01 to about 5 percent weight/volume arabic acid; up to 20 percent volume/volume ethylene glycol; up to 1 percent weight/volume sodium azide; and a buffer having a pH of from about 7 to about 10 and a molarity of about 0.001 to about 3. More preferably, the electrophoretic gel of the instant invention comprises from about 0.7 to about 1.2 percent weight/volume high electroendosmosis agarose; from about 0.5 to about 1.5 percent weight/volume arabic acid; from about 1 to about 10 percent volume/volume ethylene glycol; from about 0.05 to about 0.15 percent weight/volume sodium azide; and a buffer having a pH of from about 8 to about 9 and a molarity of from about 0.05 to about 1. Optimally, the electrophoretic gel of the instant invention comprises about 1 percent weight/volume high electroendosmosis agarose; about 1 percent weight/volume arabic acid; about 5 percent volume/volume ethylene glycol; about 0.1 percent weight/volume sodium azide; and a barbital buffer having a pH of about 8.6 and a molarity of about 0.05.

The electrophoretic gels of the instant invention can be prepared via any technique well known to those skilled in the art. See, for example, Cawley, supra. In general, the gel solution is prepared by mixing the various ingredients present therein while heating the mixture to a temperature of about 80° to about 100° C. The electrophoretic gel can be prepared by either standard molding or casting techniques. The gels can be stored at any convenient temperature, for example from about 2° to about 40° C., preferably from about 18° to about 26° C. It is preferred to store the electrophoretic gels in sealed, plastic trays until ready for use.

Samples can be applied to the electrophoretic gels of the instant invention via any technique used in the prior art, e.g., via a microliter syringe. The electrophoretic gels can be electrophoresed at 100 volts for 20 minutes. If desired, the gels can be fixed in an alcohol:acetic acid mixture such as 60 percent reagent alcohol, 30 percent deionized water, and 10 percent glacial acetic acid. In addition, the gels can optionally be dried at about 80° to about 90° C.

The following examples are provided for the purpose of further illustration only and are not intended to be limitations on the disclosed invention.

EXAMPLE 1

The two electrophoretic gel formulations set forth in Table I were each employed in the following protocol in order to demonstrate the improved electrophoretic technique of the instant invention for separating serum proteins and the improved electrophoretic gel for use therein. The sole difference between the two electrophoretic gels employed in this comparative experiment was that the electrophoretic gel within the scope of this invention contained arabic acid, i.e., a specific acid polysaccharide, whereas the electrophoretic gel outside of the scope of this invention was devoid of any acid polysaccharide.

PROTOCOL

Electrophoretic Procedure 1.0 A serum sample was applied to the surface of the gel via a template method.
2.0 The gel was electrophoresed in barbital buffer, pH 8.6.
3.0 The gel was placed in a fixative solution comprising deionized water, ethyl alcohol, and glacial acetic acid (3:6:1) until precipitated and observed.

The results obtained from the above protocol for each gel formulation of Table I are also set forth in Table I.

TABLE I

| Ingredients | Electrophoretic Gel Within Scope of Instant Invention | Electrophoretic Gel Outside Scope of Instant Invention |
|---|---|---|
| 1% wt/v agarose (high electroendosmosis) | X | X |
| 1% wt/v arabic acid | X | — |
| 0.1% wt/v sodium azide | X | X |
| 5% v/v ethylene glycol Barbital buffer, pH 8.6 ± 0.1 at 20–25° C.; ionic strength 0.05 | X | X |
| Serum Protein Fixation Time (t), Minutes | t<3 | t>30 |

As the serum protein fixation times of Table I demonstrate, an electrophoretic technique for separating serum proteins employing the improved electrophoretic gel of the instant invention is capable of fixing serum proteins in less than 3 minutes. In contrast, a similar technique differing solely in that the electrophoretic gel employed therein was devoid of any acid polysaccharide (wherein the acid moiety thereof comprises at least one carboxyl group) or the salts thereof was incapable of fixing the serum protein even after a 30 minute period.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. An electrophoretic gel of the type comprising a polysaccharide, characterized in that said electrophoretic gel further comprises an acid polysaccharide and salts thereof, wherein the acid moiety of said acid polysaccharide comprises at least one carboxyl group.

2. The electrophoretic gel of claim 1 wherein said acid polysaccharide is selected from a group consisting of arabic acid, tragacanth acid, khaya acid, alginic acid, pectic acid, and linseed acid.

3. The electrophoretic gel of claim 2 wherein said salts are selected from a group consisting of sodium, potassium, calcium, and magnesium.

4. The electrophoretic gel of claim 1 wherein said acid polysaccharide is arabic acid.

5. The electrophoretic gel of claim 1 further comprising a buffer having a basic pH.

6. The electrophoretic gel of claim 5 wherein said acid polysaccharide is selected from a group consisting of arabic acid, tragacanth acid, khaya acid, alginic acid, pectic acid, and linseed acid.

7. The electrophoretic gel of claim 6 wherein said salts are selected from a group consisting of sodium, potassium, calcium, and magnesium.

8. The electrophoretic gel of claim 5 wherein said acid polysaccharide is arabic acid.

9. The electrophoretic gel of claim 5 further comprising a preservative.

10. The electrophoretic gel of claim 9 wherein said acid polysaccharide is selected from a group consisting of arabic acid, tragacanth acid, khaya acid, alginic acid, pectic acid, and linseed acid.

11. The electrophoretic gel of claim 10 wherein said salts are selected from a group consisting of sodium, potassium, calcium, and magnesium.

12. The electrophoretic gel of claim 9 wherein said acid polysaccharide is arabic acid.

13. The electrophoretic gel of claim 5 further comprising an alkylpolyol having 2 to 6 carbon atoms and 2 to 4 hydroxyl groups.

14. The electrophoretic gel of claim 13 wherein said acid polysaccharide is selected from a group consisting of arabic acid, tragacanth acid, khaya acid, pectic acid, and linseed acid.

15. The electrophoretic gel of claim 14 wherein said salts are selected from a group consisting of sodium, potassium, calcium, and magnesium.

16. The electrophoretic gel of claim 13 wherein said acid polysaccharide is arabic acid.

17. The electrophoretic gel of claim 5 further comprising a preservative and an alkylpolyol having 2 to 5 carbon atoms.

18. The electrophoretic gel of claim 17 wherein said polysaccharide is selected from a group consisting of agar and agarose.

19. The electrophoretic gel of claim 17 wherein said alkylpolyol has 2 to 4 carbon atoms.

20. The electrophoretic gel of claim 17 wherein said preservative is sodium azide.

21. The electrophoretic gel of claim 17 wherein said buffer has a pH of from about 7 to about 10.

22. The electrophoretic gel of claim 17 wherein said polysaccharide is selected from a group consisting of agar and agarose; said alkylpolyol has 2 to 4 carbon atoms; said preservative is sodium azide; and said buffer has a pH of from about 7 to about 10.

23. The electrophoretic gel of claim 22 wherein said acid polysaccharide is selected from a group consisting of arabic acid, tragacanth acid, khaya acid, alginic acid, pectic acid, and linseed acid.

24. The electrophoretic gel of claim 23 wherein said salts are selected from a group consisting of sodium, potassium, calcium, and magnesium.

25. The electrophoretic gel of claim 22 wherein said acid polysaccharide is arabic acid.

26. The electrophoretic gel of claim 22 wherein said polysaccharide is high electroendosmosis agarose.

27. The electrophoretic gel of claim 22 wherein said alkylene polyol is ethylene glycol.

28. The electrophoretic gel of claim 22 wherein said buffer has a pH of from about 8 to about 9.

29. The electrophoretic gel of claim 22 wherein said polysaccharide is high electroendosmosis agarose; said alkylene polyol is ethylene glycol; said preservative is sodium azide; and said buffer has a pH of from about 8 to about 9.

30. The electrophoretic gel of claim 29 wherein said acid polysaccharide is selected from a group consisting of arabic acid, tragacanth acid, khaya acid, alginic acid, pectic acid, and linseed acid.

31. The electrophoretic gel of claim 30 wherein said salts are selected from a group consisting of sodium, potassium, calcium, and magnesium.

32. The electrophoretic gel of claim 29 wherein said acid polysaccharide is arabic acid.

33. The electrophoretic gel of claim 5 comprising:
(a) from about 0.4 to about 1.5% weight/volume high electroendosmosis agarose;
(b) from about 0.01 to about 5% weight/volume arabic acid;
(c) up to 20% volume/volume ethylene glycol;
(d) up to 1% weight/volume sodium azide; and
(e) said buffer having a pH of from about 7 to about 10 and a molarity of from about 0.001 to about 3.

34. The electrophoretic gel of claim 5 comprising:
(a) from about 0.7 to about 1.2% weight/volume high electroendosmosis agarose;
(b) from about 0.5 to about 1.5% weight/volume arabic acid;
(c) from about 1 to about 10% volume/volume ethylene glycol;
(d) from about 0.05 to about 0.15% weight/volume sodium azide; and
(e) said buffer having a pH of from about 8 to about 9 and a molarity of from about 0.05 to about 1.

35. The electrophoretic gel of claim 5 comprising:
(a) about 1% weight/volume high electroendosmosis agarose;
(b) about 1% weight/volume arabic acid;
(c) about 5% volume/volume ethylene glycol;
(d) about 0.1% weight/volume sodium azide; and
(e) said barbital buffer having a pH of about 8.6 and a molarity of about 0.05.

36. An improved electrophoretic technique for assaying the relative distribution of proteins of the type wherein a sample to be assayed is applied to an electrophoretic gel and said electrophoretic gel is electrophoresed, characterized in that said electrophoretic gel is the electrophoretic gel of any one of claims 1–34 or 35.

* * * * *